United States Patent [19]

Jackson

[11] 4,164,862
[45] Aug. 21, 1979

[54] MULTICOMPONENT THERMAL CONDUCTIVITY ANALYZER

[76] Inventor: Milton L. Jackson, Drawer 90,000 G, Houston, Tex. 77090

[21] Appl. No.: 854,817

[22] Filed: Nov. 25, 1977

[51] Int. Cl.$^2$ ............................................. G01N 25/18
[52] U.S. Cl. ................................................... 73/27 R
[58] Field of Search ....................................... 73/27 R

[56] References Cited

U.S. PATENT DOCUMENTS

| 3,429,178 | 2/1969 | Durbin | 73/27 R |
| 3,603,147 | 9/1971 | Dorman | 73/204 |

FOREIGN PATENT DOCUMENTS 840159  7/1960  United Kingdom ................. 73/27 R Primary Examiner—James J. Gill
Attorney, Agent, or Firm—Gunn & Lee

[57] ABSTRACT

Apparatus for measurement of gases in a multiple component gas stream or sample is disclosed. A regulated pressure system delivers the gas to N thermal conductivity type detectors utilizing wheatstone bridges. The thermal conductivity detector utilizes a resistance heated element (one leg of the bridge) which heats a chamber, and the sample flow varies the heat by thermal conduction in the chamber. The circuit creates a feedback signal for purposes of stabilizing the temperature in the chamber at a specified level. As the feedback signal is varied as a result of the change in concentration in the sample flow, this change in feedback signal is a signal which is related to the input. The apparatus utilizes N wheatstone bridges and feedback circuits for a sample gas having N constituents which are operated at N distinct temperatures relative to one another, and the respective output signals from the N detector circuits have the form of N simultaneous equations to form an output signal indicative of the gas makeup of the N gases in the sample.

13 Claims, 2 Drawing Figures

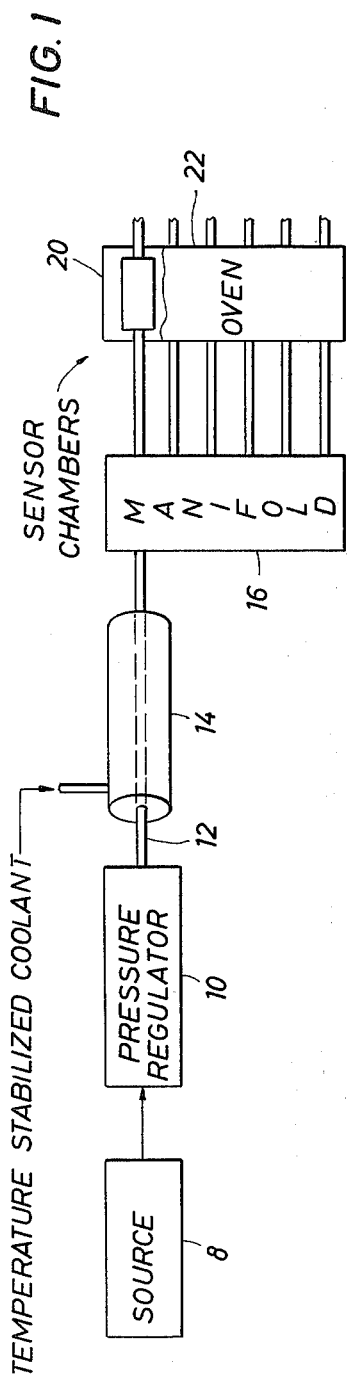
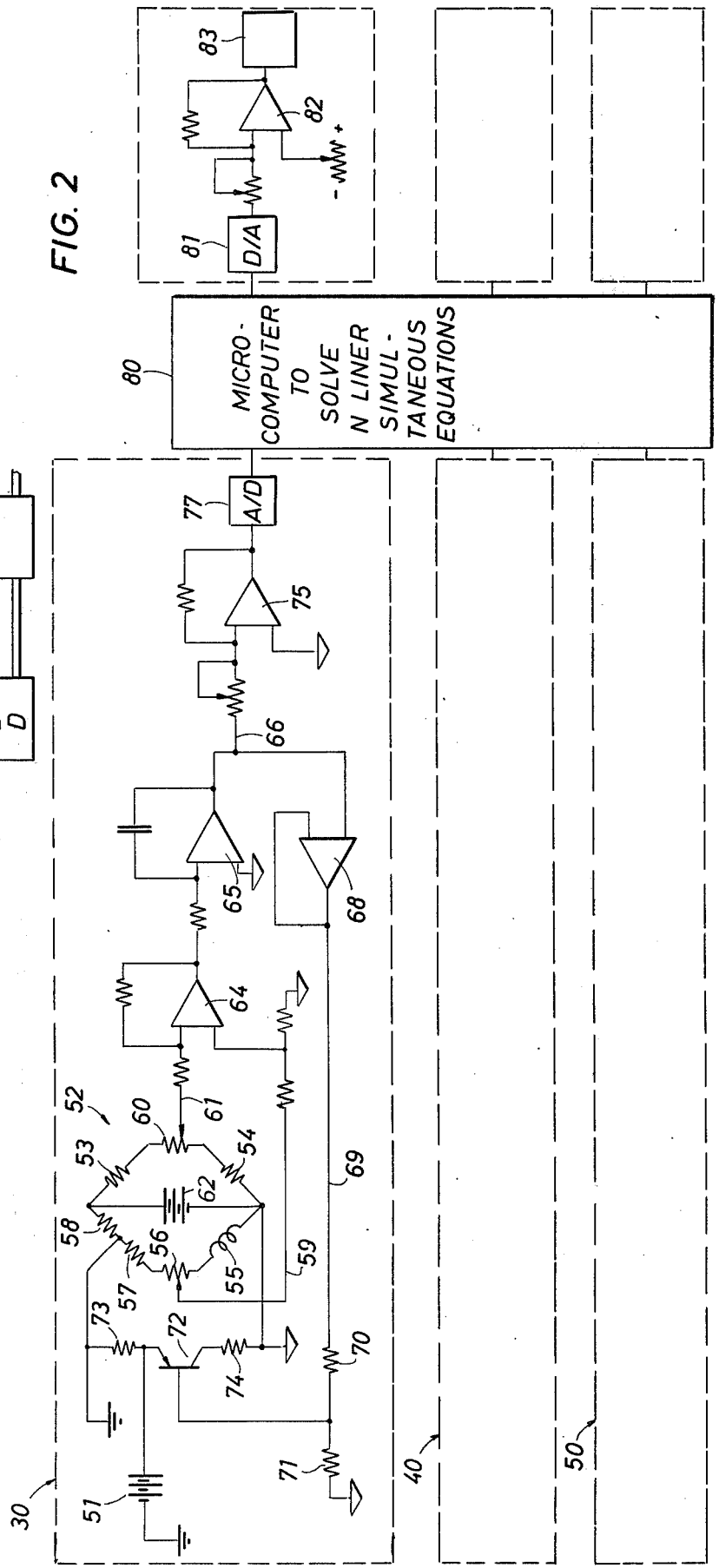
FIG. 1
FIG. 2

MULTICOMPONENT THERMAL CONDUCTIVITY ANALYZER

PRIOR ART

Examples are the MSA Thermatron Analyzer as advertised in bulletin No. 0716-8; Hays Thermal Conductivity Analyzer; Bendix Process Gas Chromatograph; Honeywell Process Gas Chromatograph; Beckman Process Gas Chromatograph; page 6–134 of *Process Instruments and Control Handbook*, published by McGraw-Hill, edited by Douglas M. Considine; and other references.

BACKGROUND OF THE DISCLOSURE

Chromatographic analysis of gas flows is an essential analytical tool. Chemical process equipment and control systems often require chromatographic analysis to control and manipulate the chemical process equipment. It is necessary in many processing plants to have some analysis of the feed stream or some other source. Analysis of the feed stream is an important preliminary step to manipulate and set the process control equipment.

An easy example is the connection of a chromatographic analyzer to the feed stream of gas supplied to a natural gas separator. In this instance, the feed stock may comprise a variable percentage of constituents of differing values which ought to be separated to obtain optimum recovery from the feed stream.

It has been discovered that each of the gases which comprise the feed stream have their own particular thermal conductivity at a given temperature. Yet, thermal conductivity bridges have been used primarily in the past to measure the thermal conductivity for analysis of the constituent gases already separated by chromatograph columns in multicomponent feed streams.

One of the earliest analytical instruments was a thermal conductivity analyzer. A two component gas stream mixture is referenced to a pure gas of one of two gas components. Two detectors in a wheatstone bridge circuit respond to concentration of the components in the mixture. The concentration change is read as a voltage change on the wheatstone bridge output.

The thermal conductivity analyzer as an analytical tool has been used only for binary type analysis, a severe handicap that has limited its popularity. Very few gas streams are binary, limiting thermal conductivity analyzers.

The many gas streams in gas processing and refining plants such as the feed stream mentioned above are often analyzed by chromatographic analysis. Chromatographic batch techniques normally involve the use of a highly precise metering device where a specified quantity of sample is delivered. The sample passes through a packed column where the migratory movement of the gas molecules enables separation into constituent components which flow in sequence past a transducer. The transducer is typically a thermal conductivity detector. This type detector often uses a very light gas such as helium to reference the gases in the mixture. The chromatograph is capable of multicomponent analysis of a sample mixture.

The MSA device mentioned above is a typical continuous flow process instrument. However, it utilizes a continuous flow of a reference gas. Thus, it must have two inputs. The incorporation of added equipment to obtain the signal from the reference gas inevitably increases the cost, increases the complexity and decreases the flexibility of the apparatus. Further, the technique of matching against a reference gas normally involves a two-gas system which is limited in the ordinary course.

CONCEPT OF THE PRESENT INVENTION

The present apparatus and method take advantage of the relationship existing between the thermal conductivity and concentration of N constituents in the specimen. The present invention utilizes the relationship given by the following equation.

$$K_s = 0.01\,(k_1 P_1 + k_2 P_2 + \ldots + k_n P_n)$$

where
- $K_s$ = thermal conductivity of the specimen
- $k_1, k_2 \ldots k_n$ = thermal conductivity for each constituent of n constituents in the samples
- $P_1, P_2 \ldots P_n$ are respective by concentrations of n constituents, volume percentage.

The difficulty with the above equation is that it includes multiple unknowns. In the event that a three-component sample gas is to be tested and measured, three separate measuring systems are used as taught by this invention.

A constant scale or numerical factor exists between a given detector electrical output signal at a specified temperature for a given gas. This factor remains constant without regard to the concentration of the gas in the mixture. A different constant, however, describes the relationship if the detector is at a different temperature. Thus, utilizing the form of equation shown above, different constants must be utilized if the detector is at a different temperature. For a specimen having three constituent gases, this then forms three equations in three unknowns with nine coefficients. The three unknowns are the concentrations of the three gases of interest. The nine coefficients are the coefficients of thermal conductivity at different temperatures. The coefficients of thermal conductivity are measured by initial calibration techniques and, being known, define three equations in three unknowns. This mathematical system is readily easily solved.

BRIEF DESCRIPTION OF THE PRESENT APPARATUS

This apparatus incorporates a thermal conductivity resistance heated detector element in a chamber or oven where the resistance detector is located in a wheatstone bridge circuit. Feedback circuitry is incorporated to vary the current flow through the wire to maintain temperature stabilization. As the sample gas is flowed past the detector, the current required to continue temperature stability in the oven is varied to form the feedback signal to balance the bridge and to further serve as an output signal of the bridge. For a sample having N constituent gases, N bridge circuits are utilized, each with its own oven operated at a relatively different temperature. Taking into account initial values set into each bridge by way of beginning calibrations when setting up the equipment, the equipment forms N output signals from the N circuits which can be solved in N simultaneous equations to provide the measure of each of the N constituent gases in the specimen. A method is also disclosed.

BRIEF DESCRIPTION OF THE DRAWINGS

FIG. 1 shows the system of the present apparatus whereby temperature stabilized gas is provided to the equipment; and FIG. 2 is a schematic wiring diagram of an apparatus for measuring three constituent gases in a sample.

DETAILED DESCRIPTION OF THE ILLUSTRATED APPARATUS

Attention is first directed to FIG. 1 of the drawings. In FIG. 1, the numeral 8 identifies a source which is a source of gas to be measured. It is a sample of N constituent gases, where N is a whole number integer. The constituent gases are mixed together to form the sample or specimen to be measured or tested. The precise makeup or nature of the specimen is not subject to any practical limitation other than to include N constituents. It will be recognized that N can be varied to different whole numbers, and, of course, the equipment taught by the present disclosure is modified to accommodate variations in N. In any case, the source delivers gas to a pressure regulator 10. The regulator 10 stabilizes the gas pressure at a known consistent pressure level. The pressure level is fixed. The pressure level is held steady to remove one of the variables from the system, namely, pressure variations. If the gas pressure were not regulated, the change in flow would produce some change in the temperature coefficients. The coefficients are dependent on pressure in varying measure in a lesser or greater degree. Pressure, temperature, flow rate and chamber configuration are factors which are not critical in the general concept, and they are preferably selected and held fixed to a specified level so that these factors do not enter into operation of the system.

The pressure regulator has an outlet line 12 which is connected then to a heat exchanger 14. A temperature stabilized fluid is introduced to the heat exchanger 14 to stabilize the temperature at a specific level. The line 12 is then input to a manifold 16 which divides the gas flow into several outlet conduits. The particular number is not critical. It is, however, important to have at least N lines from the manifold 16. The manifold 16 delivers the gas at the specified temperature and pressure to sensor chambers indicated generally at 20. They are located in an oven 22. Thereafter, the sample can be vented or flared. Ordinarily, the total flow volume through the equipment is quite small in comparison with the throughput of the system being tested.

The equipment described and shown appears somewhat expensive. This is not necessarily required. The back pressure can be atmosphere pressure to eliminate a back pressure valve. The regulator can be simple or complex dependent on the pressure of the source. As an example, the specimen source may have a pressure of 5000 psi. Regulation down to 50 psi. requires more expensive equipment than a drop of 100 psi. Also, a large drop cools the specimen more than a small drop, and, therefore, the heat exchanger may be more complex. In some instances, the heat exchanger can be omitted if the gas flow temperature is reasonably well stabilized. The pressure at the detector inlet is only a few inches of water.

Attention is next directed to FIG. 2 of the drawings where the schematic illustrates a system for measuring concentrations of three gases in a sample. Three is strictly arbitrary, and the number could be different. In this event, the circuits shown in FIG. 2 would be duplicated so that there is one each for each constituent.

In FIG. 2 of the drawings, there are three circuits incorporated for a three-constituent gas, and the three gases are conveniently labeled as gases A, B and C. These arbitrary designations will be utilized in identifying the mathematical terms necessary to understand the present invention. The N simultaneous equations are written in the symbols A, B and C to identify the components which are associated with the three unique gases in the sample.

In FIG. 2, the numeral 30 identifies the first apparatus of the N sets of identical apparatus. They are identical in construction. They differ in the operating temperature and in the initial conditions which are adjusted or set into the equipment. The adjustments will be described hereinafter. The operating temperatures of the three different systems are arbitrarily selected to provide three different operating temperatures. This particular apparatus, having three components, tests the gas flowing through it at the specified temperature levels. The three identical bridge circuits thus each are exposed to the same sample, and they all work at different temperatures. This provides enough spread in the calibration points so that no two of the bridges are operated at the same temperature level. Redundant operation of two circuits is not needed except to provide error checking means. It will not be considered hereafter.

Because the bridge circuits are all identical, one will be described in detail, and its description can be extended to the others. In the operation of the present invention, the manner of calibration will be set forth specifically later on.

In FIG. 2 of the drawings, the numeral 51 identifies a power supply which is connected to a bridge 52. The bridge 52 includes four legs. One is a fixed resistor 53. Another leg is a second fixed resistor 54. The detector leg is 55. It is connected in series with an adjustable resistor 56, a fixed resistor 57 and another fixed resistor 58. The adjustable resistor 56 includes a wiper arm which is connected to a conductor 59. It is arranged oppositely in the bridge from an adjustable resistor 60 which is also connected to a wiper arm and an output conductor 61. A power supply 62 is connected across the corners of the bridge to provide power for its operation.

The resistor 55 is exposed to the flowing gas. It is maintained in an insulated chamber, otherwise known as an oven, and the gas flows through the oven. The bridge is thus provided with power from the supply 62. This power forms two branch currents flowing through the two respective paths connected across the power supply. The current flow across the bridge is set in one path (resistors 53 and 54). It is manipulated in the other leg by variations in the thermal conductivity of the gas.

It will be recalled that the gas flowing past the detector 55 contributes to heat removal along with other fixed factors. To the extent that heat is removed at a variable rate from the oven surrounding the detector element 55, the current flow in the element fluctuates. When it fluctuates, it forms a temperature dependent current signal. This current signal is output through the conductor 59. After the variable resistor 56 has been set, the conductor 59 in conjunction with the conductor 61 both provide input signals for a differential amplifier 64. The amplifier is provided with suitable feedback so that it is a high input impedance device and is relatively linear in operation. It connects to another amplifier 65.

The amplifier 65 forms an output signal at the node 66. The output signal is supplied to output circuitry to be described. The output signal is also supplied to a feedback loop.

The bridge circuit incorporates a feedback path utilizing an amplifier 68 which forms an output signal on a conductor 69 which is input through a series dropping resistor 70 and coupled to a resistor 71. The resistors 70 and 71 serve as a voltage divider. The feedback signal is input to the base of a transistor 72. The transistor is connected to a power supply 51, and it selectively shuts current from the power supply 51 to resistors 73 and 74. The transistor 72 is thus controllably gated to thereby vary the current flowing through the detector 55.

One important feature of this invention is the feedback circuit. Briefly, a specified beginning current through the detector creates ohmic heat which is carried away at a rate dependent on the gas stream. The rate is dependent on the composite or weighted average coefficient of thermal conductivity which is, in turn, dependent on the weighted thermal conductivity of each of N constituents. The feedback circuit varies the current flow through the detector 55 to increase or decrease the heat liberated by it. The heat liberated must vary to seek a stabilized temperature at the detector 55. Therefore, the variations in feedback current are proportional to the composite coefficient of thermal conductivity as it varies. The total current flowing through the detector 55 is the sum of two currents, one attributed to the power supply 62 and the other current flowing from the supply 51 as varied by the transistor 72. This latter current is, in turn, dependent on the feedback signal.

The voltage indication input on the conductors 59 and 61 to the amplifier 64 remains substantially the same. The differential signal, markedly amplified, is formed at the node 66. This incremental voltage signal is indicative of and proportional to the change in current required to maintain temperature stability. Accordingly, the isolation amplifier 68 couples the signal to the transistor 72 in the described manner, and it, in turn, adjusts the current through the detector 55 to achieve temperature balance.

The bridge output signal is coupled through an amplifier 75 and is input to an analog to digital converter 77. It, in turn, forms an input to a microcomputer 80. The microcomputer is constructed and arranged, typically with a PROM, to receive and store the necessary program for solving N linear simultaneous equations with N variables. In the example shown, it is provided with three inputs, and it solves three equations for the three unknowns representative of the three gases.

The microcomputer is connected to an output digital to analog converter 81 which, in turn, is input to an amplifier 82 for forming an analog signal on a strip chart recorder 83. It will be observed that where the gas analysis system is used for three unknowns in the sample gas that three separate analog to digital converters are required at 77, and three separate digital to analog converters are required at 81. It is possible to use a single high speed converter in each instance and multiplex the inputs. The microcomputer 80 can operate so much more rapidly than is necessary that the computing speed of the equipment provides excessively rapid computation. Alternately, the analog valves can be input to an analog computer, thereby avoiding the use of analog to digital or digital to analog converters.

Prior to operation, the device is set up in the following manner. Each bridge is zeroed or calibrated using a pure gas sample which is the same as one of the gases to be analyzed. Zeroing is accomplished at the particular temperature for the bridge assigned to it. The flow rate is also fixed by use of the pressure regulator. The pure gas sample flows across the detector 55, and the adjustment of the variable resistors 56 and 60 is made to achieve a zero output voltage. This is done for all three of the systems.

The first step in the method of the present invention is to determine the numerical values of the thermal conductivity factor for each bridge. First of all, gas A in a pure state is flowed across the three detectors. Again, pressure is held constant, and the temperature for each detector is held constant at the selected levels. Three output voltages are recorded. The same calibration is repeated for gases B and C. An example of the voltage readings could easily be as follows.

|  | Bridge 30 | Bridge 40 | Bridge 50 |
|---|---|---|---|
| Pure Gas A | 1.210 | 1.051 | 0.921 |
| Pure Gas B | 0.700 | 0.555 | 0.401 |
| Pure Gas C | 0.520 | 0.410 | 0.321 |

Utilizing the equation first quoted above, it can be written three times in terms of the variables A, B and C. One then obtains the following three equations.

$$1 A + \frac{0.700}{1.210} B + \frac{0.520}{1.210} C = V_1$$
$$1 A + \frac{0.555}{1.051} B + \frac{0.410}{1.051} C = V_2$$
$$1 A + \frac{0.401}{0.921} B + \frac{0.321}{0.921} C = V_3$$

The coefficients of the terms B and C, above, are cumbersome, and they are reduced by simple arithmetic to yield the following set of nine coefficients.

$$1 A + 0.578 B + 0.430 C = V_1$$

$$1 A + 0.528 B + 0.390 C = V_2$$

$$1 A + 0.435 B + 0.349 C = V_3$$

The original null or zero adjustment can be selected to reduce the mathematical complexity of the simultaneous equations. If certain values are zero (achieved by initial calibration), then the data is easier to compute. Consider a three gas sample with different zero values:

|  | Bridge 30 | Bridge 40 | Bridge 50 |
|---|---|---|---|
| Pure Gas A | 0 | 3.05 | 3.85 |
| Pure Gas B | 3.82 | 0 | −0.10 |
| Pure Gas C | 2.67 | 0.62 | 0 |

If these values are input as coefficients to three simultaneous equations, one will have:

$$0.0 A + 3.05 B + 3.85 C = V_1$$

$$3.82 A + 0.00 B - 0.10 C = V_2$$

$$2.67 A + 0.62 B + 0.00 C = V_3$$

The foregoing calibration provides nine coefficients. There are three gases passing over each detector, and, in addition, there are three different detectors. Each system is different because the temperature of the detector is maintained at a different level. The nine coefficients are input into memory in the computer 80. They serve as calibration factors for the computer. As long as the same pressures and temperatures are maintained with the same three gases, the coefficients are useful and will apply to repetitive measurements.

With the equations given above, the three equations can be used to solve for the three unknowns which are the measures of the three variables in the system.

If the sample mixture provides values of $V_1$, $V_2$ and $V_3$ are 2.68, 0.32 and 0.80 volts, respectively, then gases A, B and C can be solved. Solving these equations, and expressing the answers in percent molarity, one obtains 19.8%, 63.6% and 16.6% for the respective gases A, B and C.

The arrangement described above can be extended to accommodate four or more variables. This extension would require the utilization of N detectors operated at N different temperatures, and it would require further the solution of N linear simultaneous equations in the manner taught. N is a whole number integer.

The analyzer of this disclosure involves no reference gas and no carrier gas and is otherwise able to achieve high quality analysis. The analyzer can give real time multiple outputs for N variables. Sharpness in definition is increased by going to larger voltage differentials and greater temperature differentials between detectors.

The foregoing is directed to the preferred embodiments of the present invention, but the scope thereof is determined by the claims which follow.

I claim:

1. A method of solving for the relative concentrations of constituents in a specimen where the constituents have different coefficients of thermal conductivity and the number of constituents is represented by N, the method comprising the steps of:
   (a) conducting a specified flow of the sample past a thermal conductivity detector means in a chamber which means is maintained at a specified temperature in a testing circuit which circuit forms an output signal $V_N$ proportional to the rate at which heat in said detector means is varied with changes in thermal conductivity and which output signal is obtained during the flow of the specimen therepast;
   (b) obtaining a set of N calibration output signals $C_N$ from pure cnstituents of the specimen flowing past the detector means;
   (c) operating a chamber and associated detector means at N different temperature levels to obtain therefrom $N \times N$ calibration output signals $C_{NN}$ on flowing the specified flow of sample therepast;
   (d) solving N simultaneous equations to obtain the relative measures of N constituents in the specimen by using the output signals and calibration signals in the following relationship:

$$V_1 = C_{11} A + C_{12} B \ldots$$
$$V_N = C_{N1} A + C_{N2} B \ldots$$

2. The method of claim 1 including the step of regulating the pressure drop and flow rate past the sensing element.

3. The method of claim 2 including the step of inputting the sample flow through a pressure regulator, heating the specimen to a specified temperature level, and controlling the pressure drop across the chamber.

4. The method of claim 1 wherein the detector means is connected in a wheatstone bridge circuit and the bridge circuit is calibrated for an initial condition determined by flowing a pure constituent thereacross at the specified temperature level, operating the bridge circuit with a feedback loop injecting current from the feedback loop into the detector means to controllably modulate the temperature thereof toward a fixed level and wherein the output signal is thereafter supplied to a computer means which calculates the constituent components in the specimen utilizing N simultaneous equations in N variables where each variable is one of the constituent gases.

5. The method of claim 1 including the step of initially calibrating the thermal detector means to a selected value prior to the step of obtaining a set of output signals for the individual constituents.

6. The method of claim 1 wherein a computer means solves N simultaneous linear equations in N variables utilizing the signals to obtain the relative measure of the constituents.

7. Apparatus for determining the relative makeup of N gaseous constituents in a flowing specimen, the apparatus comprising a bridge circuit having one leg thereof exposed to a flowing specimen, the leg including a resistance element detector means which is exposed to a specimen flow wherein the specimen flow varies the heat liberated by the resistance element detector means, and further including a feedback circuit connected to the output of said bridge circuit which provides a feedback current connected for flow through said detector means to stabilize the temperature thereof and wherein the feedback signal represents the variations in thermal conductivity experienced by said detector means and wherein there are N such circuits and each of said circuits provides an input voltage to a computer means constructed and arranged to solve N simultaneous linear equations in N variables and wherein each variable has a coefficient determined by flowing the pure constituent of the specimen respectively past said detector means adapted to be operated at different temperatures.

8. The apparatus of claim 7 wherein said detector means is a heated wire in a chamber with a means for introducing the specimen flow therepast.

9. The apparatus of claim 7 wherein the bridge is a wheatstone bridge circuit connected to include said detector means as one leg thereof and a power supply connected to flow current across said detector means.

10. The apparatus of claim 9 including a variable resistor in said bridge with an adjustable tap for adjusting said bridge.

11. The apparatus of claim 9 including a second power supply and first means controllably supplying current therefrom to said detector means dependent on a feedback signal from said feedback circuit to said first means and wherein said feedback circuit is provided with the output signal across said bridge.

12. The apparatus of claim 7 including a four-sided bridge, one side including said detector means and another side including a fixed reference standard.

13. The apparatus of claim 12 including a current amplifier means connected with said detector means and having an input connected with said feedback signal.

* * * * *